United States Patent
Lu et al.

(10) Patent No.: US 10,831,346 B2
(45) Date of Patent: Nov. 10, 2020

(54) ERGONOMIC AND SENSOR ANALYSIS BASED USER EXPERIENCE DESIGN

(71) Applicant: International Business Machines Corporation, Armonk, NY (US)

(72) Inventors: Fang Lu, Billerica, MA (US); Nadiya Kochura, Worcester County, MA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/174,425

(22) Filed: Oct. 30, 2018

(65) Prior Publication Data

US 2020/0133450 A1  Apr. 30, 2020

(51) Int. Cl.
| | |
|---|---|
| *G06F 3/00* | (2006.01) |
| *G06F 3/0484* | (2013.01) |
| *G06K 9/00* | (2006.01) |
| *G06F 8/77* | (2018.01) |
| *G06F 9/451* | (2018.01) |
| *G06F 3/01* | (2006.01) |
| *G06F 3/033* | (2013.01) |

(52) U.S. Cl.
CPC .............. *G06F 3/0484* (2013.01); *G06F 8/77* (2013.01); *G06F 9/451* (2018.02); *G06K 9/00302* (2013.01); *G06F 3/033* (2013.01)

(58) Field of Classification Search
CPC . G06F 3/484; G06F 9/451; G06F 8/77; G06F 9/00302
See application file for complete search history.

(56) References Cited

U.S. PATENT DOCUMENTS

| | | | |
|---|---|---|---|
| 8,335,876 B2 | 12/2012 | Davenport et al. | |
| 10,275,046 B2* | 4/2019 | Zhang | G06F 21/34 |
| 10,514,727 B2* | 12/2019 | Seo | G06F 1/3265 |
| 10,551,928 B2* | 2/2020 | Mistry | G06F 3/0481 |
| 2013/0235073 A1* | 9/2013 | Jaramillo | G09G 5/00 345/619 |
| 2013/0344859 A1* | 12/2013 | Abramson | H04M 1/72577 455/418 |
| 2014/0337841 A1* | 11/2014 | Hyde | H04W 52/0229 718/1 |

(Continued)

FOREIGN PATENT DOCUMENTS

| | | |
|---|---|---|
| EP | 2515526 A2 | 10/2012 |
| WO | 2017180367 A1 | 10/2017 |

*Primary Examiner* — Nicholas Augustine
(74) *Attorney, Agent, or Firm* — Patterson + Sheridan, LLP (57) ABSTRACT

Ergonomic and sensor analysis based user experience design improvement is provided in various embodiments by: detecting interactions between a user and an element of a user interface of a software application executing on a computing device; gathering biometric data for the user from interface devices of the computing device; identifying a task performed in the software application that corresponds to the interactions and associates the biometric data with the interactions; adjusting a user interface setting for the element to reduce a strain on the user, wherein the user interface setting comprises at least one of: a location of the element relative to a second element of the user interface involved in the task; a relative size of the element in the user interface; a color balance of the element; and a size and location of a hitbox of the element for registering user selection of the element.

17 Claims, 10 Drawing Sheets

(56) References Cited

U.S. PATENT DOCUMENTS

| | | | |
|---|---|---|---|
| 2015/0248235 A1* | 9/2015 | Offenberg | G06F 3/017 |
| | | | 715/773 |
| 2015/0312404 A1* | 10/2015 | Abramson | H04M 1/72569 |
| | | | 455/418 |
| 2017/0235365 A1 | 8/2017 | Siripurapu et al. | |
| 2017/0279957 A1* | 9/2017 | Abramson et al. | |
| | | | H04M 1/6075 |
| 2018/0074694 A1* | 3/2018 | Lehmann | G06F 3/0414 |
| 2019/0080189 A1* | 3/2019 | Van Os | G06K 9/00288 |

* cited by examiner

ERGONOMIC AND SENSOR ANALYSIS BASED USER EXPERIENCE DESIGN

BACKGROUND

The present invention relates to user experience improvement in software systems, and more specifically, to gathering ergonomic and sensor data to affect the improvement. Users of software programs interact with those programs via physical devices, such as monitors and displays that output visual information to the user, speakers that output audio information, haptic devices that output tactile information, controllers that accept tactile input (e.g., keyboards, touch screens, mice/trackballs/trackpads), microphones that accept audio input, and cameras that accept visual input. The arrangement of these physical components in the physical environment may impart strains on the user when using the software program, which may be exacerbated by the layout or accessibility of elements of the software program.

SUMMARY

According to one embodiment of the present invention, a method for ergonomic and sensor analysis based user experience design improvement is provided, the method comprising: detecting interactions between a user and a first element of a user interface of a software application executing on a computing device; gathering biometric data for the user from interface devices of the computing device; identifying a task performed in the software application that corresponds to the interactions and associates the biometric data with the interactions; in response to determining that a strain on the user when performing the task exceeds an ergonomic threshold, adjusting a user interface setting for the first element to reduce the strain, wherein the user interface setting comprises at least one of: a location of the first element relative to a second element of the user interface involved in the task; a relative size of the first element in the user interface; a color balance of the first element; and a size and location of a hitbox of the first element for registering user selection of the first element.

According to one embodiment of the present invention, a computer readable medium including instructions that when executed by a processor enable the processor to perform an operation for ergonomic and sensor analysis based user experience design improvement is provided, the operation comprising: detecting interactions between a user and a first element of a user interface of a software application running on a computing device; gathering biometric data for the user from interface devices of the computing device; identifying a task performed in the software application that corresponds to the interactions and associates the biometric data with the interactions; in response to determining that a strain on the user in performing the task exceeds an ergonomic threshold, adjusting a user interface setting for the first element to reduce the strain, wherein the user interface setting comprises at least one of: a location of the first element relative to a second element of the user interface involved in the task; a relative size of the first element in the user interface; a color balance of the first element; and a size and location of a hitbox of the first element for registering user selection of the first element.

According to one embodiment of the present invention, a system for ergonomic and sensor analysis based user experience design improvement is provided, the system comprising: a processor; and a memory storage device, including instructions that when executed by the processor enable the system to: detect interactions between a user and a first element of a user interface of a software application running on a computing device; gather biometric data for the user from interface devices of the computing device; identify a task performed in the software application that corresponds to the interactions and associates the biometric data with the interactions; in response to determining that a strain on the user in performing the task exceeds an ergonomic threshold, adjust a user interface setting for the first element to reduce the strain, wherein the user interface setting comprises at least one of: a location of the first element relative to a second element of the user interface involved in the task; a relative size of the first element in the user interface; a color balance of the first element; and a size and location of a hitbox of the first element for registering user selection of the first element.

DETAILED DESCRIPTION

The present disclosure provides for User Experience (UX) design improvements via ergonomic and sensor analysis. Although design teams may seek to provide a UX that is optimized for most users performing most tasks in a software application, some users may find the originally provided UX to be non-optimal (e.g., due to hardware or physical constraints, due to performing atypical tasks, or due to not being familiar with the interface). Embodiments of the present disclosure gather data related to an application's use of text, images, and audio to evaluate the current position and actions of the user to determine when repetitive motions, eye focus, body position, and other ergonomic measures for the user may be improved by adjusting the UX of the application. These data may be forwarded to the design team for later use in redesign of the application, or may affect local options for the application to improve the UX for the particular user.

Figure 1A:
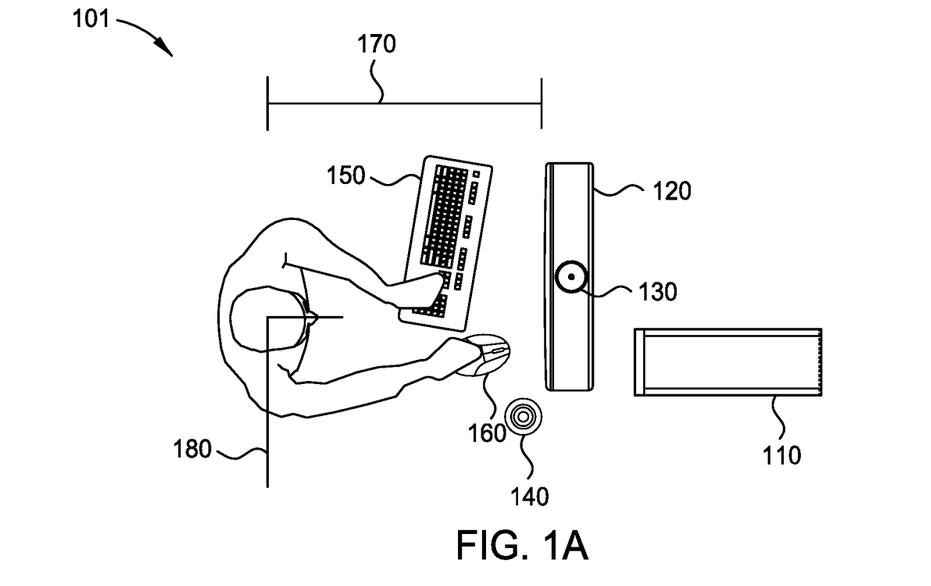
FIGS. 1A-C illustrate use cases for a computing device, according to embodiments of the present disclosure.
Figure 1B:
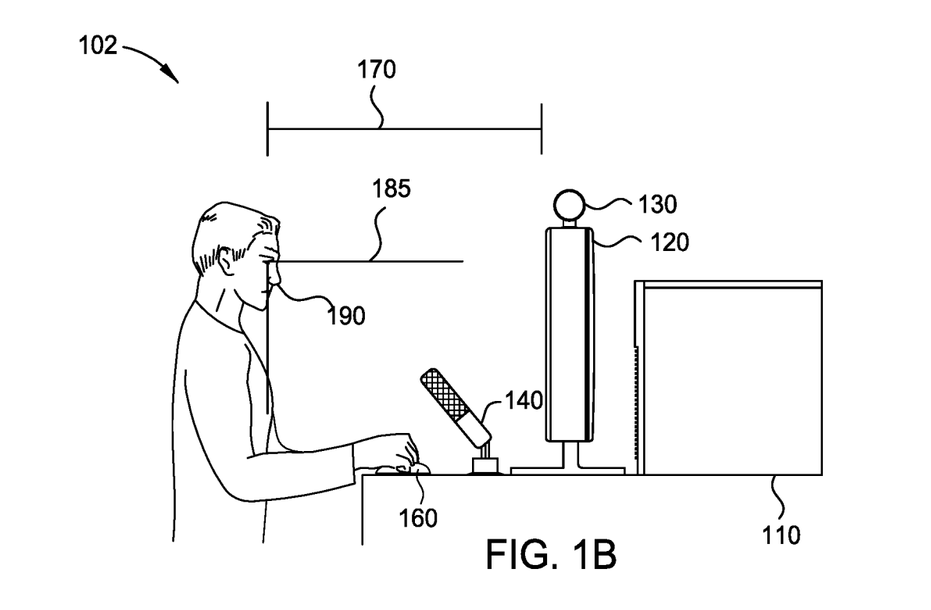
Figure 1C:
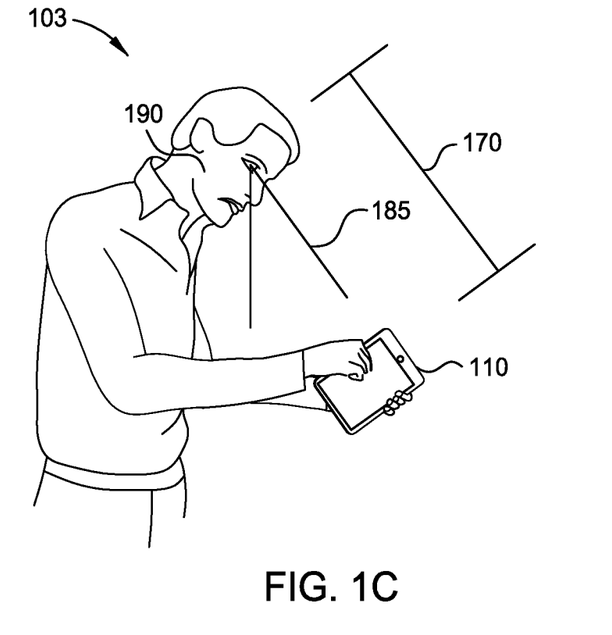

FIGS. 1A and 1B illustrate two viewpoints for a first use case 101 for a user interacting with a computer 110 running a software application. FIG. 1C illustrates a viewpoint for a second use case 102 for a user interacting with a computer 110 running a software application. The user interacts with the software application by various physical input and output devices, such as, for example, a display device 120, a camera 130, a microphone 140, a keyboard 150, a pointing device 160 (e.g., a mouse, a trackball, a touch screen), etc. The input/output devices may be separate from the computer 110 (as per FIGS. 1A and 1B) or may be integrated in the computer 110 (as per FIG. 1C). Other input/output devices, more input/output devices, or fewer input/output devices may be provided in other embodiments.

The input devices include various sensors to receive inputs from the user and to measure various conditions of use that are collectively referred to as biometric data. For example, a keyboard 150 may include various switches to record when a particular key has been pressed by the user, and to measure the force at which the user presses the particular key. In another example, a camera 130 includes software for measuring a distance 170 between the user's eyes and the display device 120, angles 180 and 185 at which the user's head is rotated relative to the user's body in various planes, and software for identifying a facial expression 190. In a further example, a pointing device 160 includes pressure sensors, to measure how hard the user is pressing various buttons on the pointing device, and an accelerometer, to measure how quickly the user moves the pointing device 160 (e.g., via a trackball, scroll wheel, or via whole-mouse movement).

As will be appreciated, the position of portions of the user relative to the display device 120 and input devices may affect the comfort of the user in using the computer 110, especially during prolonged use sessions. For example, the angle at which the user's arms and wrists are held may ease or exacerbate joint or tendon discomfort. Similarly, the distance 170 and angles 180, 185 of the user relative to the display device 120 may influence whether the user experiences neck or eye strain. However, the positions, arrangements, and color balances (including contrasts, brightnesses, and hue schemas) of various elements presented on the display device 120 may encourage or require the user to perform more frequent actions, longer actions, and actions in non-optimal postures than is comfortable in the course of completing a task, thereby defeating an otherwise ergonomically optimized physical layout for using the computer 110. For example, a poorly chosen font size or color versus a background may encourage a user to lean in closer to the display device 120 than a well-chosen font size or color. In another example, elements of a user interface separated by a larger distance may require larger real-world motions to select than elements separated by a smaller distance.

The actions performed by the user may include both gross motor movements (e.g., moving an arm to affect a movement of a pointing device 160 or rotating or extending a neck to track the head) and fine motor movements (e.g., moving a finger to affect a click, key press, or button hold; squinting the eyes; or tracking the eyes) to affect an interaction in the software or to observe actions taken in the software. Actions performed by the user may also include actions taken in response to or independent from the actions intended to interact with software (e.g., a facial expression coinciding with a software effect; cracking joints to release pressure after performing interactive actions; stretching; leaving workspace including the computer 110). Sensors included in various input devices track these user actions in relation to software tasks to improve the design of the user experience.

Figure 2:
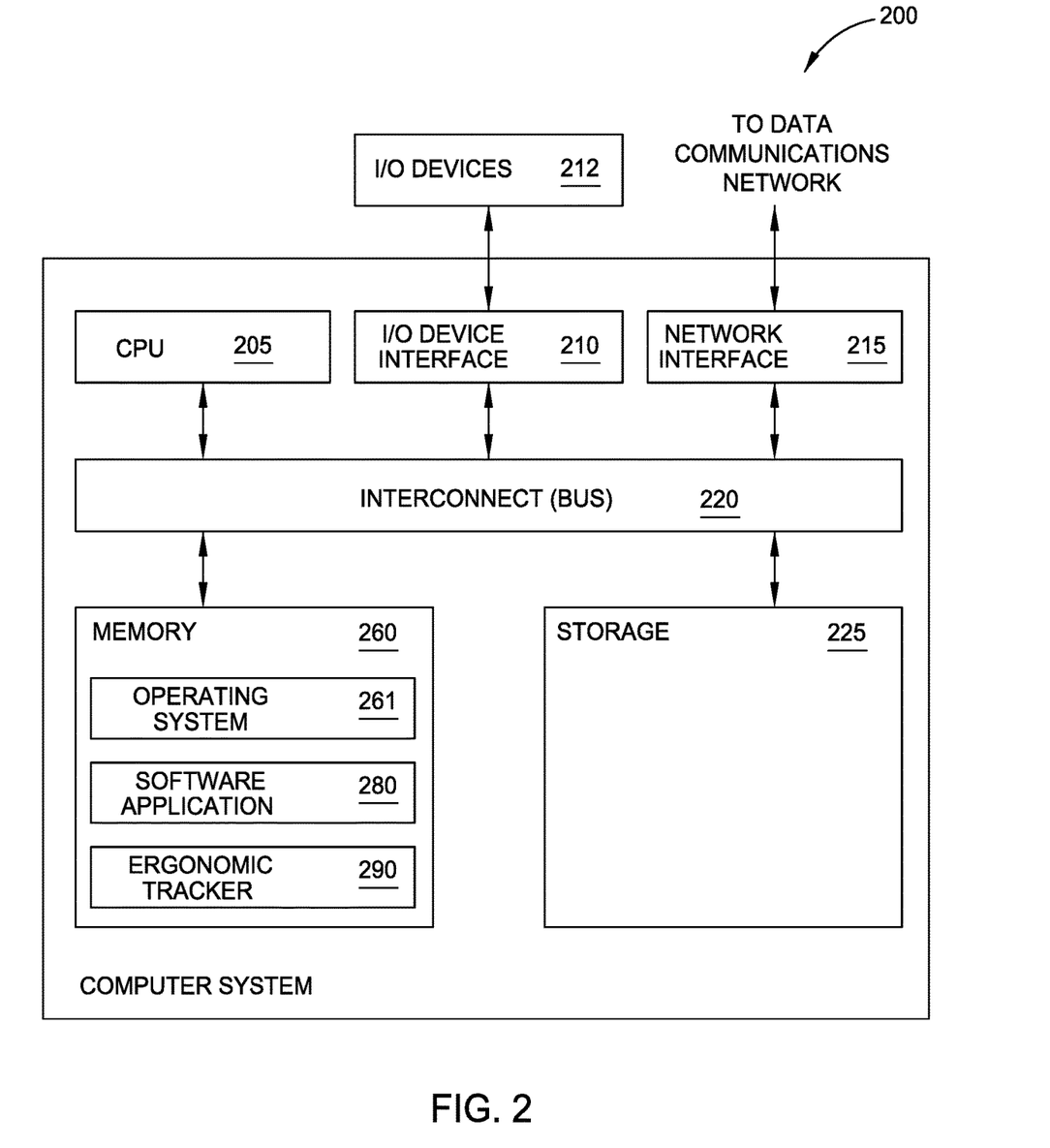
FIG. 2 illustrates a computing system, according to embodiments of the present disclosure.

FIG. 2 illustrates a computing system 200, such as computer 100, which may be a personal computer, a laptop, a tablet, a smartphone, etc. As shown, the computing system 200 includes, without limitation, a central processing unit (CPU) 205, a network interface 215, an interconnect 220, a memory 260, and storage 230. The computing system 200 may also include an I/O device interface 210 connecting I/O devices 212 (e.g., keyboard, display and mouse devices) to the computing system 200.

The CPU 205 retrieves and executes programming instructions stored in the memory 260. Similarly, the CPU 205 stores and retrieves application data residing in the memory 260. The interconnect 220 facilitates transmission, such as of programming instructions and application data, between the CPU 205, I/O device interface 210, storage 230, network interface 215, and memory 260. CPU 205 is included to be representative of a single CPU, multiple CPUs, a single CPU having multiple processing cores, and the like. And the memory 260 is generally included to be representative of a random access memory. The storage 230 may be a disk drive storage device. Although shown as a single unit, the storage 220 may be a combination of fixed and/or removable storage devices, such as magnetic disk drives, flash drives, removable memory cards or optical storage, network attached storage (NAS), or a storage area-network (SAN). Further, computing system 200 is included to be representative of a physical computing system as well as virtual machine instances hosted on a set of underlying physical computing systems. Further still, although shown as a single computing system, one of ordinary skill in the art will recognized that the components of the computing system 200 shown in FIG. 2 may be distributed across multiple computing systems connected by a data communications network.

As shown, the memory 260 includes an operating system 261 (e.g., Microsoft's Windows® Operating System), at least one software application 280, and an ergonomic tracker 290 linked with the software application 280 to provide improvements of the UX for the software application 280 based on ergonomic and sensor analysis.

As the user provides inputs, the software application 280 translates those inputs into interactions within the framework of the software application 280. For example, a word processing application translates inputs from a keyboard 150 into characters in a typing interface and translates inputs from a pointing device 160 into selections of various user interface (UI) elements, such as, for example, positions in typed text, typeface options, special character insertions, file save commands, etc. In another example, an Operating System (OS) application translates inputs from a pointing device 160 to move files within a storage schema, launch selected applications, arranging UI elements within a graphical user interface (GUI), etc.

The ergonomic tracker 290 gathers the biometric data from the input devices and detects interactions in a UI of one or more software applications 280 running on the computer 110 that the ergonomic tracker 290 is linked to. The ergonomic tracker 290 associates the biometric data with the interaction data in a time series and identifies various tasks completed by a user in the software application 280.

FIG. 3A-D illustrate a series of interactions with a user interface to perform a task in a software application. The illustrated task is a drag-and-drop task that includes interactions in which the user attempts to select a first element 320a of the UI 310, drag the first element 320a to a second element 320b, and release the first element 320a over the second element 320b. However, due to non-optimized UI design, the interactions with the UI 310 may require physical actions that are more frequent (e.g., multiple attempts), longer, or more forceful that are ergonomically advisable. The present disclosure is applicable to improvements in UI design beyond drag-and-drop tasks, which is provided as a non-limiting example of how the present disclosure improves computing devices.

In FIGS. 3A-D, a UI 310 is presented with a first element 320a, a second element 320b, and a third element 320c (generally, elements 320), respective hitboxes 330a-c (generally, hitbox 330) for the elements 320a-c, and a cursor 340.

More or fewer elements 320 of different sizes, shapes, arrangements, labeling, coloring, are possible in other embodiments.

The elements 320 may include various widgets, menus, folders, icons, and software defined buttons in the UI 310 for performing various tasks or representing various files or objects. In the illustrated examples, the first element 320a is presented as a five-pointed star, the second element 320b is presented as a white folder with a label 350b of a white five-pointed start, and the third element 320c is presented as a white folder with a label 350c of a white six-pointed star.

A hitbox 330 represents the area in the UI 310 that is selectable by the user to interact with an associated element 320. In FIGS. 3A-D, the hitboxes 330 are shown via dotted lines defining an area in the UI 310, but may be invisible to the user. Hitboxes 330 may be rectangular, circular, shaped according to the associated element 320, or irregularly shaped, and may be sized to match an area of the associated element 320, extend past the associated element 320, to be smaller than the associated element 320, and may be aligned to be centered or offset from an anchor point of the associated element 320.

The cursor 340 is shown as a graphical pointer in the UI 310 that may be associated with a pointer device 160. In other embodiments, such as a computer 110 using a touch screen, the cursor 340 represents a point of contact from the user touching the touch screen, which may be shown or invisible to the user.

Figure 3A:
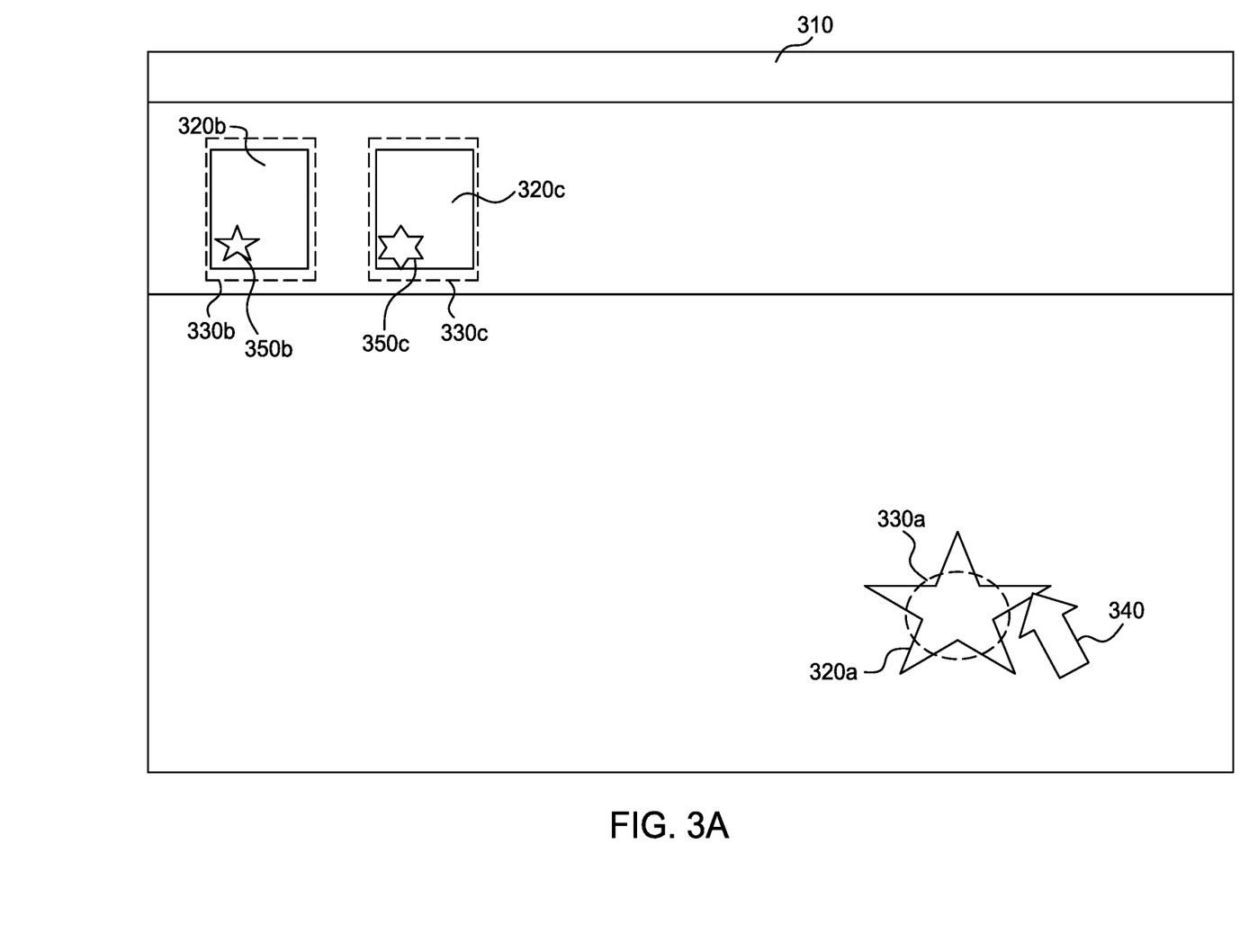
FIGS. 3A-D illustrate a user interface for which the user experience may be improved according to embodiments of the present disclosure.
Figure 3B:
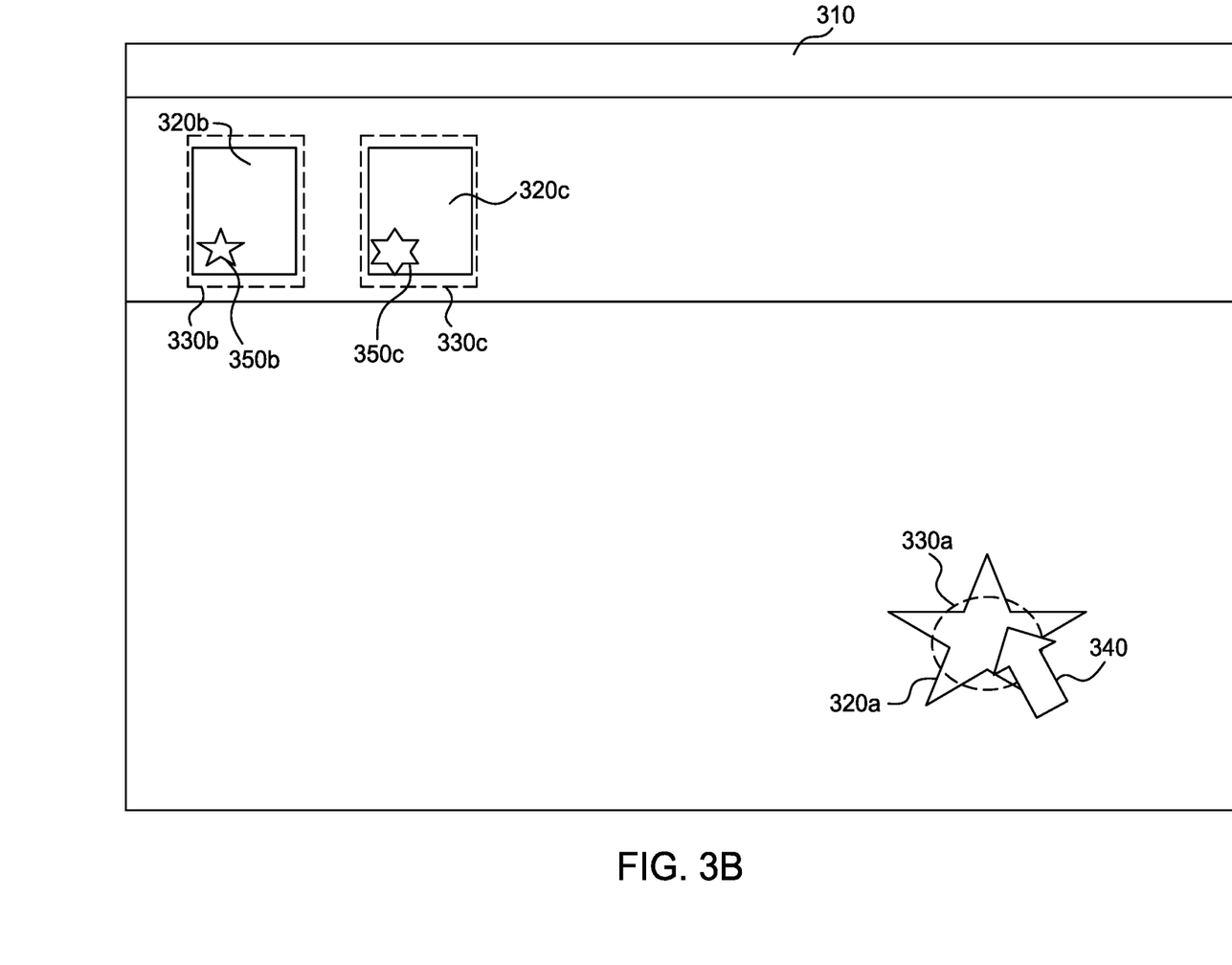

FIG. 3A illustrates the user unsuccessfully attempting to select the first element 320a, with a cursor 340 positioned on the displayed icon for the first element 320a, but not on the hitbox 330a associated with the first element 320a. FIG. 3B illustrates the user successfully attempting to select the first element 320a, with a cursor 340 positioned on the displayed icon and hitbox 330a for the first element 320a. The ergonomic tracker 290 may track the number of miss-clicks that the user needs to select the element 320 as attempted interactions that are part of a task, and track the force made during those clicks, relative locations of those clicks to the associated hitbox 330 and other hitboxes 320, the time between successive clicks, whether the click is a single click/double click/click-and-hold, a body position during the click, etc. Attempted interactions include those interactions made by the user that do not result in an interaction with the intended element 320, including actions that do not result in an interaction (e.g., a missed click, typing without focus in a document) or that select a different element 320 than is used in the following task. For example, the ergonomic tracker 290 may determines that a user who selects a first element 320a, then selects a second element 320b, and then performs a task using the second element 320b (but not the first element 320a) made an attempted interaction with the second element 320b as part of the task when the first element 320a was selected.

Figure 3C:
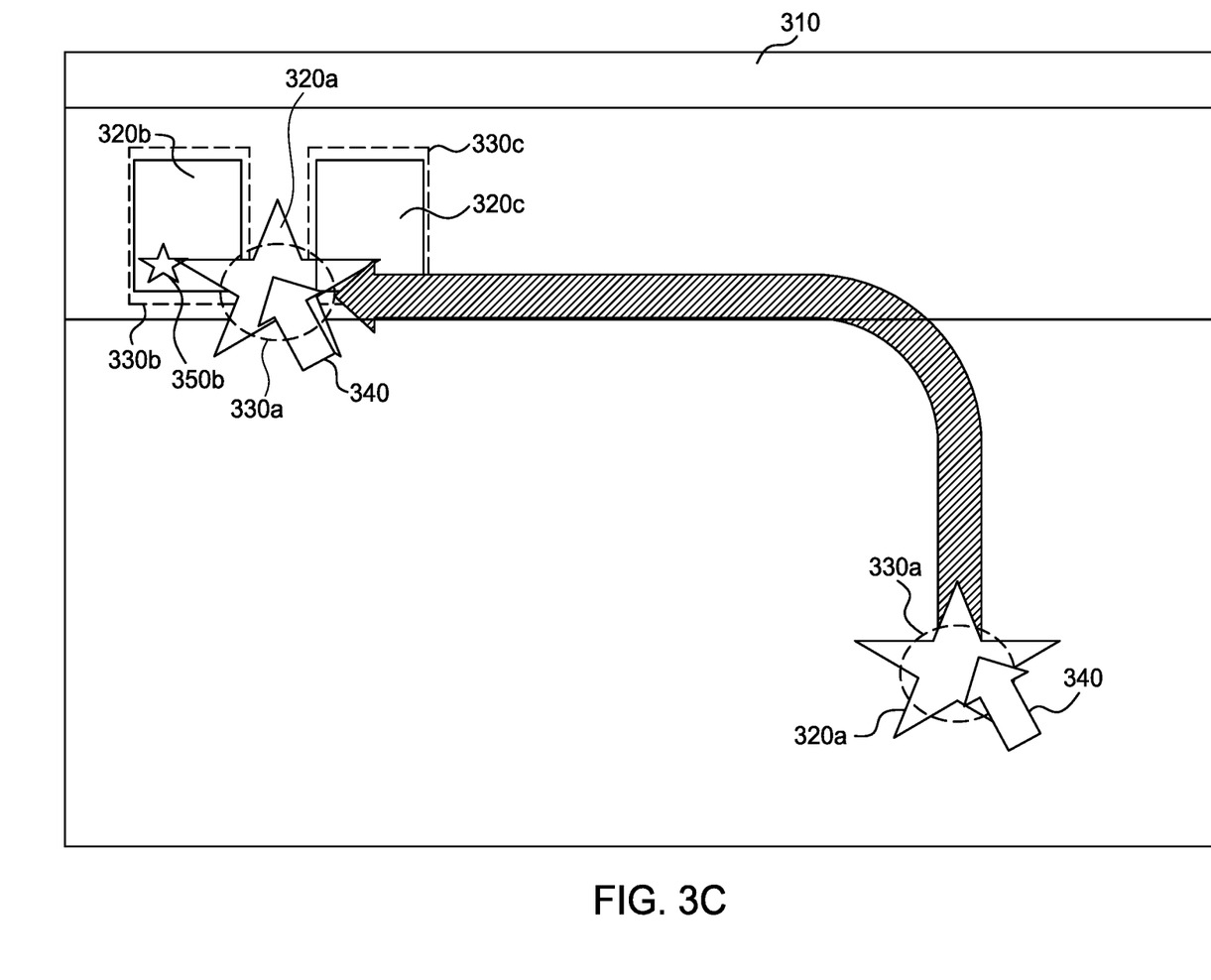
Figure 3D:
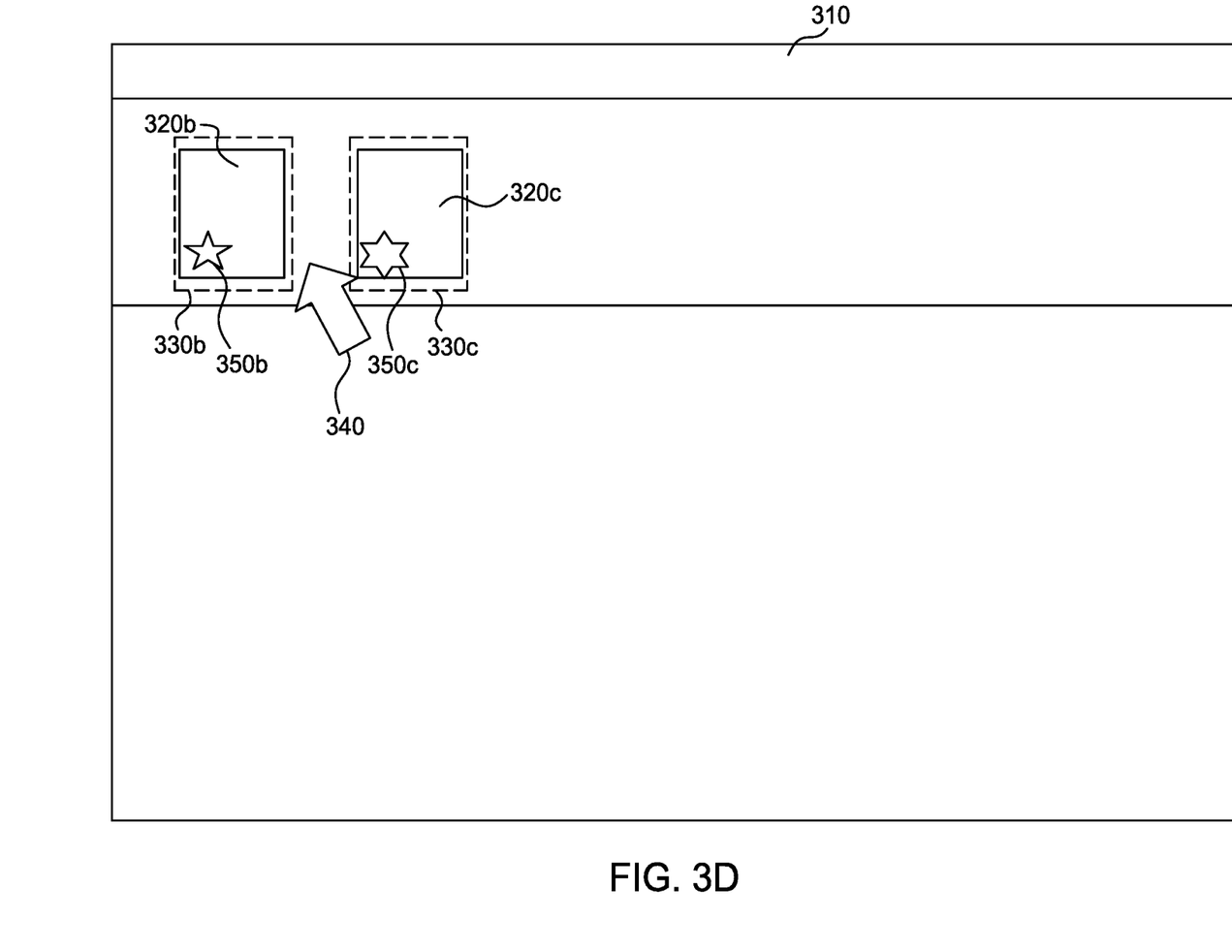

FIG. 3C illustrates the user dragging the first element 320a from an initial position to a final position over the second element 320b and the third element 320c. In the illustrated example, the second element 320b and the third element 320c are folders, that may accept and store the file represented by the first element 320 when the first element 320a is dragged over the respective hitbox 330 and de-selected (e.g., "dropped") by the user. FIG. 4D illustrates the UI 310 once the user has dropped the first element 320a into one of the folders represented by the second element 320b and the third element 320c. Due to the proximity of the folders, the user may not know which folder the first element 320a has been dropped into, and may have to access the folders to verify where the file represented by the first element 320a has been stored. The ergonomic tracker 290 may determine how far the user moves the first element 320a from the initial position to the final position within the UI 310, a speed and motion used to perform the actions in the real world required to affect the interactions in the software application 280, whether the user performs follow-up interactions (e.g., to determine which folder the file was stored in), a length of time to perform the interaction, etc.

Figure 4A:
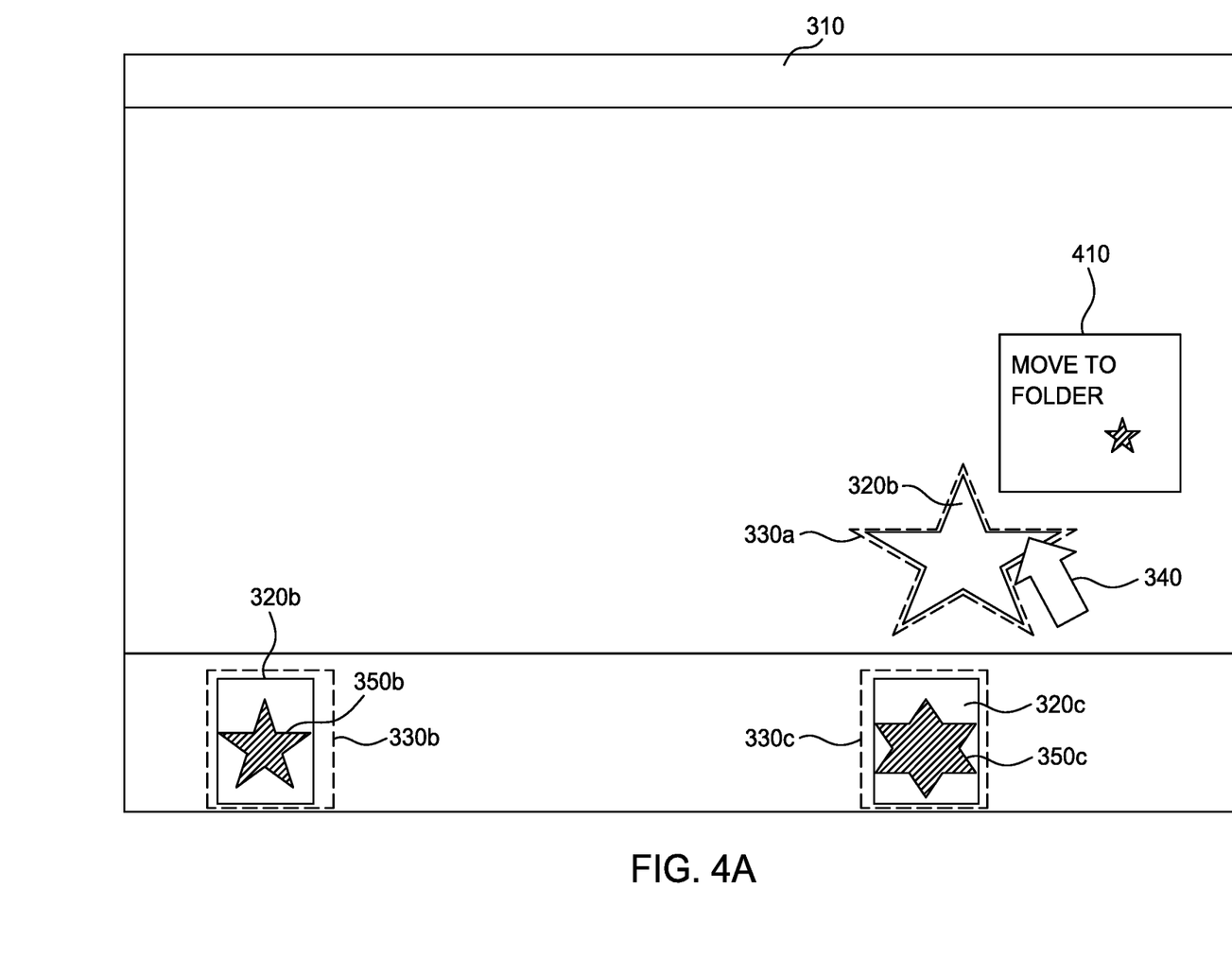
FIGS. 4A and 4B illustrate a user interface for which the user experience may have been improved according to embodiments of the present disclosure
Figure 4B:
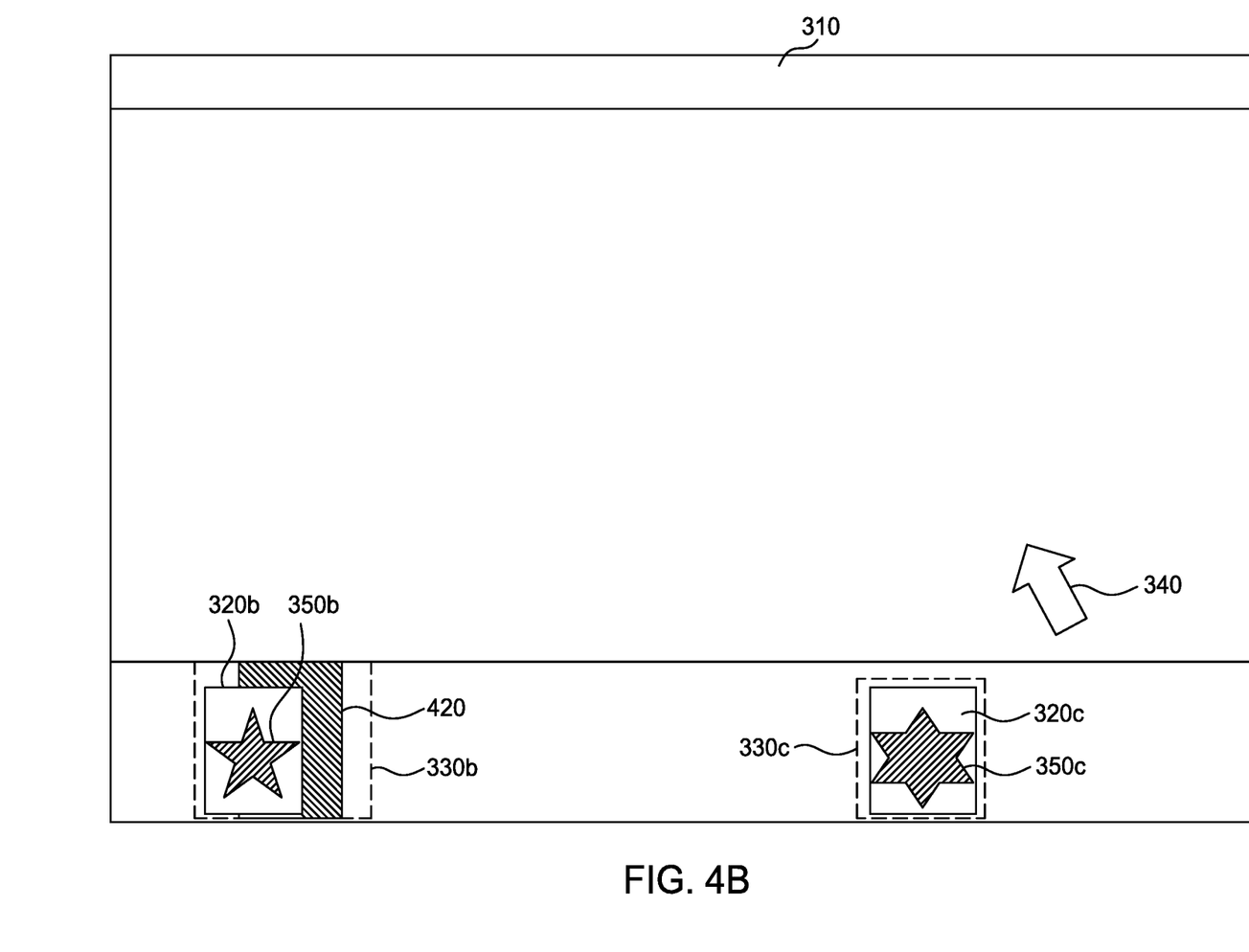

FIGS. 4A and 4B present the UI 310 as illustrated in FIGS. 3A-D that are adjusted to improve the UX thereof in performing a drag-and-drop operation, according to embodiments of the present disclosure. The UI 310 is presented with a first element 320a, a second element 320b, and a third element 320c, respective hitboxes 330a-c for the elements 320a-c, and a cursor 340. More or fewer elements 320 of different sizes, shapes, arrangements, labeling, coloring, are possible in other embodiments. Additionally, a shortcut element 410 and an indicator element 420 are presented as part of the improved UX.

In FIG. 4A, the first element 320a is presented as a five-pointed star, and the hitbox 330a thereof has been improved to match the shape of the first element 320a. In some embodiments, the ergonomic tracker 290 automatically adjusts the hitbox 330a in response to identifying user strain in attempting to interact with the hitbox 330 (e.g., more than n miss-clicks, click force over a threshold pressure). In other embodiments, the ergonomic tracker 290 notes the user strain in attempting to interact with the hitbox 330 and includes the strain determination in a strain report transmitted to the development team for the software application 280.

In FIGS. 4A and 4B, the second element 320b is presented as a white folder with a label 350b of a darker five-pointed start, and the third element 320c is presented as a white folder with a label 350c of a darker six-pointed star; increasing the contrast between the elements and associated labels 350. Additionally, the relative sizes of the labels 350 are increased relative to the associated elements 320 in increase readability. In various embodiments, the ergonomic tracker 290 automatically adjusts the color balance and/or sizing of the second and third elements 320 relative to the associated labels 350 in response to identifying user strain in attempting to interact with the second and third elements 320 (e.g., the user squinting, the user moving closer to the display device 120, the user re-doing an action). In other embodiments, the ergonomic tracker 290 notes the user strain in attempting to interact with the second and third elements 320 and includes the strain determination in a strain report transmitted to the development team for the software application 280.

The position of the second and third elements 320 are also adjusted from FIGS. 3A-D to FIGS. 4A and 4B, so that the distance between locations that the user moves the first element 320a across may be reduced. Additionally, the distance between the second and third elements 320 to reduce the likelihood of dropping the first element 320a into an undesired folder. The ergonomic tracker 290 may make the positional adjustments to the elements 320 based on identified user strain when attempting to move (e.g., drag and drop) the first element 320a to one of the second and third elements 320. Alternatively or additionally, the ergonomic tracker 290 may include the positional data for the drag and drop task in a strain report transmitted to the development team for the software application 280.

The shortcut element 410 presented in FIG. 4A is one example of the ergonomic tracker 290 providing the user with an additional control in the UI 310 to complete a task with fewer actions to thereby reduce strain on the user. For example, after identifying that the user moves the first object 320*a* to the second object 320*b*, when the user re-selects the first object 320*a*, the ergonomic tracker 290 may cause the software application 280 to display the shortcut element 410. The shortcut element 410, when selected by the user, may cause the software application to perform a specified task, with the user performing fewer or less strenuous actions to affect the task in the software application 280. For example, instead of dragging the first element 320*a* over to the second element 320*b* (including selecting, moving across the UI 310, and deselecting) the user may instead select the first element 310 and select the shortcut element 410 to store the file represented by the first element 320*a* in the folder represented by the second element 320*b*.

The indicator element 420 presented in FIG. 4B is one example of the ergonomic tracker 290 providing the user with a visual indication in the UI 310 to complete a task with fewer action to thereby reduce strain on the user. For example, after identifying that the user moves the first element 320*a* to the second element 320*b* and double checks the folder represented by the second element 320*b* actually contains the file represented by first element 320*a*, the ergonomic tracker 290 may cause the software application 280 to display the indicator element 420 in response to the user dropping an element 310 into another element 320. The indicator element 420 provided feedback to the user that a task has been performed, and may eliminate interactions from future performances of the task that the ergonomic tracker 290 (or a development team alerted by the ergonomic tracker 290) deemed as superfluous.

Figure 5:
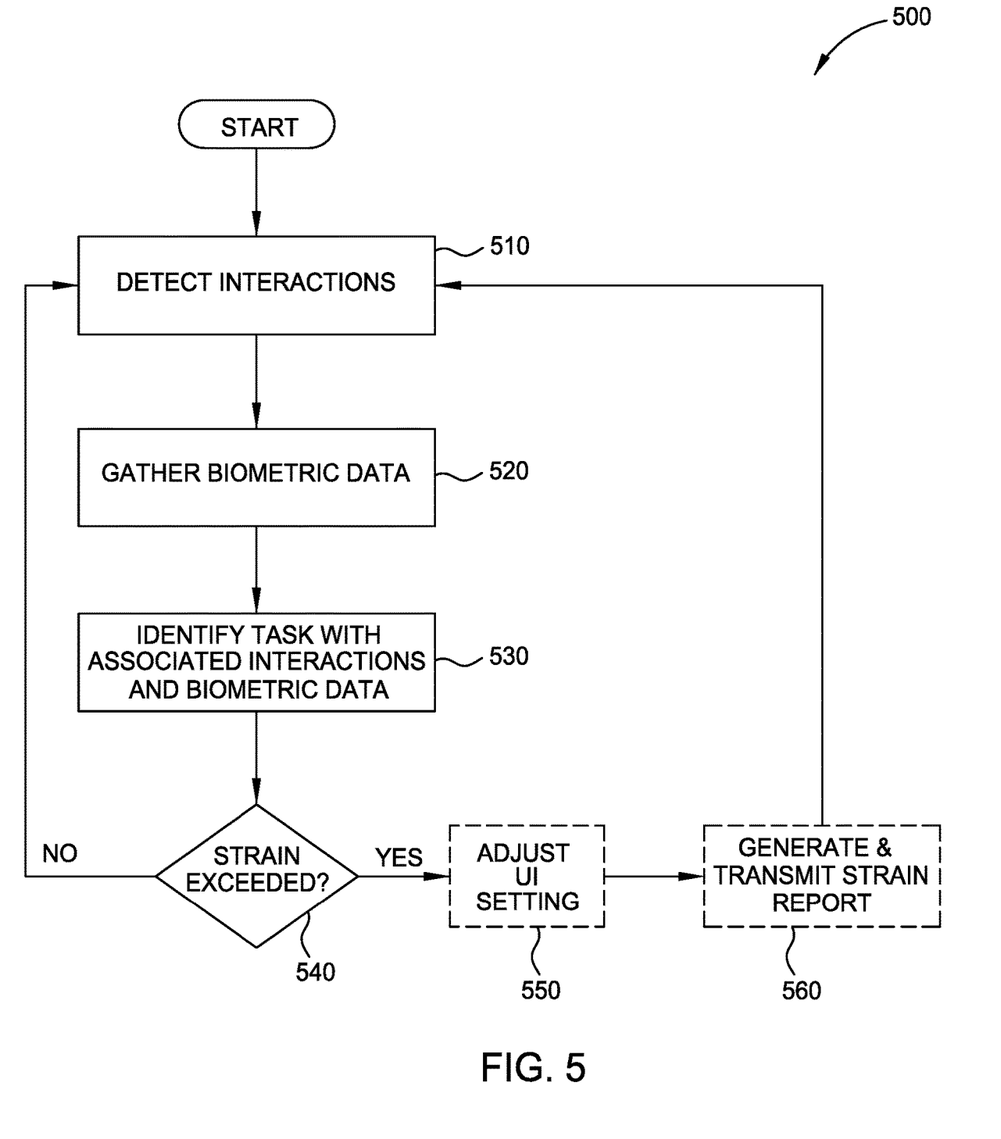
FIG. 5 is a flowchart of a method for implementing ergonomic and sensor analysis based user experience design improvements, according to embodiments of the present disclosure.

FIG. 5 is a flowchart of a method 500 for implementing ergonomic and sensor analysis based UX design improvements. Method 500 begins with block 510, where the ergonomic tracker 290 detects interactions made with a software application 280 using various input devices of a computer 110.

At block 520, the ergonomic tracker 290 gathers biometric data from various sensors associated with the input devices of the computer 110 being used by the user. The biometric data may include measurements of how many time the user clicks a button, how long the user pauses after a performance of a button click, the pressure the user applies to an input device to perform an action, how many times the user needs to drag and drop items on the UI 310, how many times/how far the user has to stretch to look the at display device 120 (e.g., in order to see the information clearly), how many times the user frowned/squinted/grimaced in front of a UI 310, how many times the user moved back and force or up and down to each direction of the screen to search for information in the UI 310, etc. The biometric data may be continuously gathered from sensors embedded in input devices and/or from cameras focused on the user.

At block 530, the ergonomic tracker 290 identifies a task performed in the software 280 and the associated biometric data and interactions performed in the software application 280 within a time window during which the task was performed. The ergonomic tracker 290 may identify distinct tasks within a series of tasks based on definitions of certain interactions in the software application 290 corresponding to a start or an end interaction for a task. For example, a selection of a particular element 320 in the UI 310 may signify a start of a task, while the selection of a different element 320 in the UI 310 may signify the end of a task. In various embodiments, the ergonomic tracker 290 may include interactions and biometric data gathered from after the end-interaction of a first task as part of the next task to capture data related to unsuccessful or strenuous attempts to start the next task. In some embodiments, the ergonomic tracker 290 may include interactions and biometric data gathered from after the end-interaction of a given task as part of the given task to capture data related to verifying the successful completion of the task.

At block 540, the ergonomic tracker 290 determines whether a strain on the user in performing the task exceeds an ergonomic threshold. In response to determining that the strain on the user is below or has not yet exceeded the ergonomic threshold, method 500 returns to block 510 for the ergonomic tracker 290 to continue monitoring the user's actions in relation to the software application 280. In response to determining that the strain on the user has exceeded the ergonomic threshold, method 500 proceeds to at least one of block 550 and block 560. As used herein, when selecting at least one element of the group of A and B, it will be understood that a selection may be only element A, only element B, or element A and element B. Stated in relation to method 500, the ergonomic tracker 290 may perform one or both of block 550 and block 560 in various embodiments in response to the strain exceeding the ergonomic threshold.

The ergonomic threshold represents one or more measures of the actions performed by the user in the real-world as translated to interactions in the software application 280 that are correlated to ranges of motion, frequencies of performance, and/or forces/speeds of performance. Each user may specify different ergonomic thresholds based on personal preference, or the ergonomic tracker 290 may develop a personalized baseline for the user based on historic user actions and an initial behavioral model. In various embodiments, the ergonomic tracker 290 may user a population-based baseline for the ergonomic thresholds until a personalized baseline is specified or developed for the user.

In one example, an ergonomic threshold may relate to a field of vision, such that an element 320 that travels more than n degrees of the user's field of vision over the UI 310 (vertically, horizontally, or both), where each user may specify a personalized value for n. In some embodiments, a field of vision ergonomic threshold may include a measure of the distance 170 between the user and a display device 120 displaying the UI 310 during performance of the task, an angle 180, 185 between the user and the display device 210, and a travel between an initial position and a final position of at least one element 320 during the task.

In one example, an ergonomic threshold may relate to a number of interactions with a pointer device 160 during performance of the task or within a predefined period of time. In a further example, a length of a drag operation of an element 320 within the UI 310 during performance of the task. In one example, a force of an action (e.g., as measured by a pressure sensor, force meter, or the like integrated with an input device) when performing of the task is used as an ergonomic threshold. In one example, an ergonomic threshold is based on a facial expression of the user, such that a pained expression, squinting, or confused expression satisfies the ergonomic threshold, while neutral, happy, or concentrating expressions do not satisfy the ergonomic threshold.

At block 550, the ergonomic tracker 290 adjusts a UI setting for the element 320 used in the task to reduce a level of strain in future performances of that task. Based on the type of ergonomic threshold exceeded (and the associated strain measured), the ergonomic tracker 290 may adjust different UI settings for the element 320. For example, when an ergonomic threshold related to eye strain, squinting, or neck strain is exceeded, the ergonomic tracker 290 may adjust the size or color balance of an element 320. In another example, when an ergonomic threshold related to arm or finger strain is exceeded, the ergonomic tracker 290 may adjust a location of the element 320 in the UI 310. In a further example, when an ergonomic threshold related to a frequency of interactions is exceeded, the ergonomic tracker 290 may adjust a size and/or a location of a hitbox 330 for an element 320.

In some embodiments, the ergonomic tracker 290 identifies tasks that are repeated by the user or that include several interactions in a multi-step task, and generates a shortcut element 410 for display in the UI 310. In one example, the shortcut element 410 is a contextual menu that allows the user to eliminate some interactions (reducing the number of clicks, drags, scrolls, etc.) to perform the task. In a further example, the shortcut element 410 is a hyperlink to text or other elements 320 elsewhere in the UI 310 so that the user is presented with relevant information in closer proximity to a current point of visual focus than the information is otherwise located in the UI 310.

In some embodiments, the ergonomic tracker 290 identifies that additional interactions are taken as part of the task, and generates an indicator element 420 to visually or audibly highlight information in the UI 310 to reduce the actions taken by the user in a future performance of the task. For example, an indicator element 420 of a chime/tone/beep, an animation, or the like may be presented to the user to highlight a UI element 320 with which the task has been performed to eliminate interactions associated with confirming the first task was completed as desired. In another example, the indicator element 420 identifies a more efficient element 310 for the user to select in the UI 310 for performing the task, so as to eliminate clicks/drags/typing or other actions by the user in performing the task.

At block 560, the ergonomic tracker 290 generates and transmits a strain report to a development team associated with the software application 280. The strain report may contain information related with which ergonomic threshold have been exceeded, a frequency at which the thresholds are exceeded, a severity by which the thresholds were exceeded, tasks performed at the time a threshold was exceeded, etc.

Method 500 may return to block 510 from block 550 or block 560 for the ergonomic tracker 290 to continue monitoring the user's actions in relation to the software application 280. The ergonomic tracker 290 may make incremental adjustments to one or more elements 320 of a UI 310 through several loops of method 500, and may batch data for inclusion in a strain report that are collected over several loops of method 500.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

The claims are as follows:

1. A method, comprising:
   detecting interactions between a user and a first element of a user interface of a software application executing on a computing device;
   gathering biometric data for the user from interface devices of the computing device;
   identifying a task performed in the software application that corresponds to the interactions and associates the biometric data with the interactions;
   in response to determining that a strain on the user when performing the task exceeds an ergonomic threshold, adjusting a user interface setting for the first element to reduce the strain by moving the first element from a first location to a second location closer relative to a second element of the user interface involved in the task;
   and
   creating a shortcut in the user interface to perform the task a second time on selection of the shortcut.

2. The method of claim 1, further comprising:
   in response to determining that the strain on the user when performing the task exceeds the ergonomic threshold, transmitting a strain report including the task and interactions related to the task to a development team associated with the software application.

3. The method of claim 1, wherein attempted interactions with the first element that do not result in actual interactions with the first element are included in the task.

4. The method of claim 1, wherein the strain on the user is determined based on:
   a distance between the user and a display device displaying the user interface during performance of the task;
   an angle between the user and the display device during performance of the task; and
   a travel between an initial position of the first element and a final position of the first element during the task.

5. The method of claim 1, wherein the strain on the user is determined based on at least one of:
   a number of interactions with a pointer device during performance of the task;
   a length of drags of the first element within the user interface during performance of the task; and
   a force of interactions with the pointing device during performance of the task.

6. The method of claim 1, wherein the strain on the user is determined based on a facial expression captured by a camera during performance of the task.

7. A computer readable medium including instructions that when executed by a processor enable the processor to perform an operation, the operation comprising:
   detecting interactions between a user and a first element of a user interface of a software application running on a computing device;
   gathering biometric data for the user from interface devices of the computing device;
   identifying a task performed in the software application that corresponds to the interactions and associates the biometric data with the interactions; and
   in response to determining that a strain on the user in performing the task exceeds an ergonomic threshold, adjusting a user interface setting for the first element to reduce the strain by moving the first element from a first location to a second location closer relative to a second element of the user interface involved in the task.

8. The computer readable medium of claim 7, further comprising:
   in response to determining that the strain on the user in performing the task exceeds the ergonomic threshold, transmitting a strain report including the task and interactions related to the task to a development team associated with the software application.

9. The computer readable medium of claim 7, wherein attempted interactions with the first element are included in the task.

10. The computer readable medium of claim 7, wherein in addition to adjusting the user interface setting for the first element, a shortcut to perform the task is created.

11. The computer readable medium of claim 7, wherein the strain on the user is determined based on at least one of:
   a number of interactions with a pointer device during performance of the task;
   a length of drags of the first element within the user interface during performance of the task; and
   a force of interactions with the pointing device during performance of the task.

12. The computer readable medium of claim 7, wherein the strain on the user is determined based on a facial expression captured by a camera during performance of the task.

13. A system, comprising:
   a processor; and
   a memory storage device, including instructions that when executed by the processor enable the system to:
      detect interactions between a user and a first element of a user interface of a software application running on a computing device;
      gather biometric data for the user from interface devices of the computing device;
      identify a task performed in the software application that corresponds to the interactions and associates the biometric data with the interactions; and
      in response to determining that a strain on the user in performing the task exceeds an ergonomic threshold, adjust a user interface setting for the first element to reduce the by moving the first element from a first location to a second location closer relative to a second element of the user interface involved in the task.

14. The system of claim 13, wherein the instructions further enable the system to:
   in response to determining that the strain on the user in performing the task exceeds the ergonomic threshold, transmit a strain report including the task and interactions related to the task to a development team associated with the software application.

15. The system of claim 13, wherein attempted interactions with the first element are included in the task.

16. The system of claim 13, wherein in addition to adjusting the user interface setting for the first element, a shortcut to perform the task is created.

17. The system of claim 13, wherein the strain on the user is determined based on:
   a distance between the user and a display device displaying the user interface during performance of the task;
   an angle between the user and the display device during performance of the task; and
   a travel between an initial position of the first element and a final position of the first element during the task.

* * * * *